United States Patent [19]

Steinstrasser et al.

[11] 3,953,491
[45] Apr. 27, 1976

[54] PHENYL ESTERS OF 4-BENZOYLOXYBENZOIC ACID

[75] Inventors: Ralf Steinsträsser; Georg Weber, both of Darmstadt, Germany

[73] Assignee: Merck Patent Gesellschaft mit beschraenkter Haftung, Darmstadt, Germany

[22] Filed: Dec. 18, 1974

[21] Appl. No.: 533,823

Related U.S. Application Data

[62] Division of Ser. No. 386,979, Aug. 9, 1973.

[30] Foreign Application Priority Data

Aug. 19, 1972 Germany............................ 2240864

[52] U.S. Cl............................ 260/465 D; 252/299; 260/465 F; 260/471 R; 260/473 R; 350/160 LC
[51] Int. Cl.²................ C07C 69/90; C07C 121/64; C07C 121/75
[58] Field of Search......... 260/465 D, 473 R, 471 R

[56] References Cited
UNITED STATES PATENTS 3,836,748   9/1974   Green et al..................... 260/473 X

*Primary Examiner*—Lewis Gotts
*Assistant Examiner*—Dolph H. Torrence
*Attorney, Agent, or Firm*—Millen, Raptes & White

[57] ABSTRACT

Nematic esters of the formula

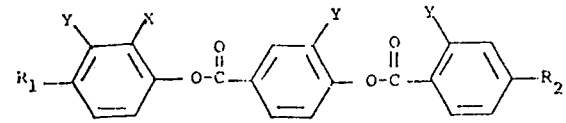

wherein $R_1$ and $R_2$ are each alkyl, alkoxyalkyl, alkoxy or alkoxyalkoxy of 1 to 10 carbon atoms, X is CN or $NO_2$ and Y is H or X which are useful for influencing the electrooptic properties of other nematic compositions.

8 Claims, No Drawings

PHENYL ESTERS OF 4-BENZOYLOXYBENZOIC ACID

CROSS-REFERENCE TO RELATED APPLICATIONS

This is a division of application Ser. No. 386,979, filed Aug. 9, 1973.

Related nematic phase compounds and compositions are described in copending, commonly assigned U.S. Pat. applications Ser. No. 91,522 filed Nov. 20, 1970 and now U.S. Pat. No. 3,773,747; Ser. No. 277,502 filed Aug. 3, 1972; Ser. No. 320,899 filed Jan. 4, 1973 and now abandoned; and Ser. No. 334,603 filed Feb. 22, 1973 and now abandoned, the contents of which are incorporated by reference herein.

BACKGROUND OF THE INVENTION

This invention relates to perpendicularly orientable nematic compounds and to the use thereof in nematic compositions and in electronic components.

Many uses of nematic compounds and compositions have been described, e.g., App. Physics Letters 13: 46 (1968) and Scientific American 222: 100 (1970), the contents of which are incorporated by reference herein; and Zeitschrift fur Naturforschung 20a: 572 (1965); 23a: 152 (1968); Osterr. Chem.-Ztg. 68: 113 (1967) (use of nematic liquid crystals in nuclear resonance spectroscopy).

Nematic substances are compounds or mixtures of compounds capable of forming an enantiotropically nematic phase, i.e., their transition point from the anisotropic to the isotropic condition (clearing point) is above their melting point. Substances which are monotropically nematic, i.e., wherein the transition point from the ansiotropic to the isotropic condition is below the melting point in the metastable range, are called nematogenic, which form an enantiotropic nematic phase only in a mixture with other nematogenic or nematic compounds.

In the development of electronic components, particularly electronic indicating devices, characterized inter alia by a flat structure and richness in image contrast compared to conventional counter or cathode-ray tubes, liquid crystals with a nematic phase have served for several years as picture screen material. These compounds display, in their nematic range i.e., the range between their melting point (m.p.) and their transition point (t.p.) a change in their light-scattering characteristic which can be controlled by AC or DC electrical fields. A prerequisite of this property, called dynamic scattering effect, is that the dipole moment of the molecule forms an angle with the longitudinal axis of the molecule.

In order to exploit this dynamic scattering effect for the production of images, a thin layer of a thickness of a few microns of a suitable nematic compound or compound mixture is placed between two electrode plates, one or both of which are transparent. If an electrical field is now applied, contrasts are produced by the change in light dispersion which can then be observed by direct frontal view or by rear viewing.

Nematic phases are utilized for converting electrical voltage pulses into optical pulses. Normally, a thin layer of liquid crystals in embedded between translucent or transparent plates having a conductive coating. An electrical voltage at the two electrodes generates in the nematic layer a microscopically visible, strong turbulence connected with a macroscopically visible intense increase in the light scattering of the electrode unit. During this process, the system becomes cloudily opaque.

The great advantage inherent in this type of electrooptic device could only be really utilized upon the discovery of nematic plates distinguished by great stability in AC and DC electrical currents and by a high chemical stability. In the meantime, a number of such nematic phases have become known, especially also those having very low-melting, wide nematic mesophase ranges.

Normally, nematic phases in a thin layer between glass or electrode plates form streaky and unoriented schlieric layers, resulting in decreased contrast of the indicator units and an unattractive appearance. Arranged in a thin layer between two glass plates or electrodes, the molecules of such phases have several possible modes of orientation. If all molecules are arranged with their longitudinal axes perpendicular to the electrode surfaces, the display device, without the application of electrical voltage, appears entirely transparent and glass-clear from any angle of observation. If the longitudinal axes of the molecules forming the nematic phase are all uniformly parallel to the glass surfaces, then transparent indicating systems are obtained when viewed from an angle of about 90°. However, at obtuse observation angles, e.g., of 45° or less, such layers exhibit a slightly cloudy appearance. In nematic phases containing azoxybenzene derivatives, this phenomenon is particularly disadvantageous because the color of the display device, dependent on the inherent yellow color of the azoxybenzene derivatives, is measurably more intense in case of a parallel orientation of the molecules than in the case of a perpendicular orientation. It is furthermore possible for the preferred direction of the molecules to be different at different locations of the display devices. In such a case, the display devices exhibit, at any angle of observation, a schlieren-permeated, irregularly turbid appearance.

Although the orientation of nematic phases between the electrodes is not decisive for the finite functioning of a display unit, perpendicularly oriented layers are preferred since, after the application of electric fields, these yield substantially better contrast under any angle of observation with respect to the areas not under voltage than do comparable nematic layers which are parallel-oriented or even inhomogeneously oriented with respect to the electrode surfaces. A process for the perpendicular orientation of nematic substances is described in U.S. Pat. application Ser. No. 334,603 filed Feb. 22, 1973.

Upon the application of an operating voltage to indicator elements filled with a perpendicularly oriented nematic liquid, a certain time period is required for turning the molecules from the vertical position into a position wherein the longitudinal axes of the molecules are arranged parallel to the electrode surfaces, since only after this has been accomplished does the dynamic scattering effect occur. The time required for this molecular orientation is prolonged at a given voltage under the influence of ultraviolet radiation, i.e., UV light undesirably increases the threshold voltage necessary for dynamic scattering, particularly when nematic substances of perpendicular orientation are employed in the indicator device.

OBJECTS OF THE INVENTION

Accordingly, it is a general object of this invention to provide novel 4,4' disubstituted phenyl esters of 4-benzoyloxybenzoic acid having nematic properties.

Another object of this invention is to provide perpendicularly orientable nematic compositions.

A further object of this invention is to provide nematic phase compositions immune to the adverse effects of ultraviolet light on their threshold voltage.

An additional object of this invention is to provide improved electrooptical display devices.

Another object of this invention is to provide a process for preparing modified nematic phase compositions which are readily orientable into a perpendicular orientation between electrode plates.

Upon further study of the specification and appended claims, further objects and advantages of this invention will become apparent to those skilled in the art.

SUMMARY OF THE INVENTION

Briefly, the above and other objects are attained in one aspect of this invention by providing a compound of the formula:

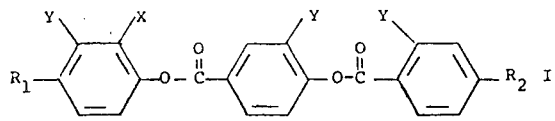

wherein $R_1$ and $R_2$ are each alkyl, alkoxyalkyl, alkoxy or alkoxyalkoxy of up to 10 carbon atoms; X is CN or $NO_2$ and Y is H or X.

DETAILED DISCUSSION

It has now been found that the effects of UV radiation on the characteristic electrooptical properties of an indicator device filled with nematic substances, especially those filled with perpendicularly oriented nematic substances, can be eliminated if certain nematic esters are added to these nematic substances. While not wishing to be bound by any theory of the invention, it appears that the essential factor is that these novel esters contain polar substituents of a strongly electronegative or electropositive character, whereby the proportion of the electric dipole moment of the molecule the vector of which is perpendicular to the longitudinal axis of the molecule is increased.

Accordingly, one aspect of the present invention relates to modified nematic mixtures which are characterized by containing 1-35%, preferably 5-15% by weight of at least one ester of the Formula 1:

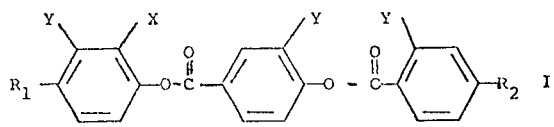

wherein $R_1$ and $R_2$ are each alkyl, alkoxyalkyl, alkoxy or alkoxyalkoxy groups of up to 10 carbon atoms; X is CN or $NO_2$ and Y is H or X.

The novel esters of this formula are 4,4'-disubstituted phenyl esters of 4-benzoyloxybenzoic acid. They possess at least one strongly polar substituent X adjacent to the ester group, preferably to the phenolic portion of the ester group, which substituent affects the dipole moment of the molecule.

It is also possible to utilize esters containing several such polar groups (substituent $Y = X$), since it appears that one need only ensure that these further substituents are arranged so that their dipole moments act approximatey in the same direction as the dipole moment of the X substituent. Thus, on the phenyl ring carrying the substituent X, a further polar substitution can only take place in the o-position to X. It will be advisable in many cases, due to difficulties in various production techniques, to utilize only phenyl esters of benzoyloxybenzoic acid substituted by one X residue. For a given application, care must be taken that the melting point of the compounds substituted by several X residues is not unduly increased, and the transition or clearing point is not unduly reduced to an extent that the desired final properties of the nematic mixture is impaired.

The structure of the residues $R_1$ and $R_2$ in the novel esters of this invention is not as critical as the structure and positioning of the residues X and Y. $R_1$ and $R_2$ can be identical or different and preferably represent straight-chain alkyl or alkoxy groups which can respectively be substituted by alkoxy groups. Normally, those esters will be employed, the chain length of which does not exceed 10 carbon atoms. Insofar as branched residues are utilized, the only further requirement is that the C atom directly joined to the phenyl ring carry at least 2 hydrogen atoms. Further substitution of $R_1$ and/or $R_2$ by alkoxy residues can be obtained particularly simply on alkoxy substituents $R_1$ or $R_2$, and compounds with identical residues, e.g., ethoxyethoxy, can be prepared in a particularly easy manner.

Insofar as the residues $R_1$ and/or $R_2$ represent alkyl groups, unbranched residues are preferred; suitable such residues include but are not limited to methyl, ethyl, n-propyl, n-butyl, n-pentyl, n-hexyl, n-heptyl, n-octyl, n-nonyl and n-decyl. Suitable alkoxy residues include but are not limited to methoxy, ethoxy, propoxy, butoxy, pentyloxy, hexyloxy, heptyloxy, octyloxy, nonyloxy and decyloxy.

Preferred esters according to the formula are those meeting one or more of the following criteria:
 a. Compounds in which X is CN;
 b. Compounds in which Y is H;
 c. Compounds in which at least one of $R_1$ and $R_2$ is straight chain alkyl of 1–10 carbon atoms, preferably 1-6 carbon atoms;
 d. Compounds in which at least one of $R_1$ and $R_2$ is straight chain alkoxy of 1–10 carbon atoms, preferably 1-6 carbon atoms;
 e. Compounds in which at least one of $R_1$ and $R_2$ is a branched alkyl or alkoxy wherein the carbon atom thereof directly joined to the phenyl ring bears two hydrogen atoms, i.e., is a secondary carbon atom;
 f. Compounds in which at least one of $R_1$ and $R_2$ is straight chain alkoxyalkoxy of two or more identical alkoxy units
 g. Compounds in which $R_1$ is straight chain alkyl of 1 - 6 carbon atoms $R_2$ is straight chain alkoxy of 1 – 6 carbon atoms, and X is CN.
 h. Compounds in which $R_1$ is n-butyl or n-pentyl, $R_2$ is straight chain alkoxy of 1 – 6 carbon atoms, and X is CN.
 i. Compounds in which $R_1$ is n-butyl or n-pentyl, $R_2$ is a straight chain alkoxy of 1 - 6 carbon atoms, X is CN and Y is H.

Compounds of the present invention, in addition to those shown in the examples, include but are not limited to:

(4'-n-butyl-2'-cyanophenyl) ester of 4-(4-n-hexyloxybenzoyloxy)benzoic acid,
(4'-n-butyl-2'-cyanophenyl) ester of 4-(4-methoxybenzoyloxy)benzoic acid,
(4'-n-butyl-2'-cyanophenyl) ester of 4-(4-ethoxyethoxybenzoyloxy)benzoic acid,
(4'-n-butyl-2'-cyanophenyl) ester of 4(4-n-butylbenzoyloxy)benzoic acid,
(2'-cyano-4'-methoxyphenyl) ester of 4-(4-n-hexyloxybenzoyloxy)benzoic acid,
(2'-cyano-4'-methoxyphenyl) ester of 4-(4-methoxybenzoyloxy)benzoic acid,
(2'-cyano-4'-methoxyphenyl) ester of 4-(4-ethoxyethoxybenzoyloxy)benzoic acid,
(2'-cyano-4'-methoxyphenyl) ester of 4-(4-n-butylbenzoyloxy)benzoic acid,
(2'-cyano-4'-n-hexyloxyphenyl) ester of 4-(4-n-hexyloxybenzoyloxy)benzoic acid,
(2'-cyano-4'-n-hexyloxyphenyl) ester of 4-(4-methoxybenzoyloxy)benzoic acid,
(2'-cyano-4'-n-hexyloxyphenyl) ester of 4(4-ethoxyethoxybenzoyloxy)benzoic acid,
(2'-cyano-4'-n-hexyloxyphenyl) ester of 4-(4-n-butylbenzoyloxy)benzoic acid,
(2'-cyano-4'-n-nonylphenyl) ester of 4-(4-n-hexyloxybenzoyloxy)benzoic acid,
(2'-cyano-4'-n-nonylphenyl) ester of 4-(4-methoxybenzoyloxy)benzoic acid,
(2'-cyano-4'-n-nonylphenyl) ester of 4-(4-ethoxyethoxybenzoyloxy)-benzoic acid,
(2'-cyano-4'-n-decylphenyl) ester of 4-(4-n-butylbenzoyloxy)-benzoic acid,
(2'-cyano-4'-n-pentylphenyl) ester of 4-(4-methoxybenzoyloxy)-benzoic acid,
(2'-cyano-4'-n-pentylphenyl) ester of 4-(4-hexyloxybenzoyloxy)-benzoic acid,
(2'-cyano-4'-n-pentylphenyl) ester of 4-(4-ethoxyethoxybenzoyloxy)-benzoic acid,
(2'-cyano-4'-n-pentylphenyl) ester of 4-(4-n-butylbenzoyloxy)-benzoic acid,
(4'-n-butyl-2'-nitrophenyl) ester of 4-(4-n-hexyloxybenzoyloxy)-benzoic acid,
(2',3'-dicyano-4'-methoxyphenyl) ester of 4-(4-n-butylbenzoyloxy)-benzoic acid,
(4'-n-butyl-2'-cyanophenyl) ester of 4-(4-n-hexyloxybenzoyloxy)-3-cyanobenzoic acid,
(2''-cyano-4''-n-hexyloxyphenyl) ester of 4-(2'-cyano-4'-methoxybenzoyloxy)-benzoic acid,
(4''-n-butyl-2''-cyanophenyl) ester of 4-(2'-cyano-4'-hexyloxybenzoyloxy)-3-cyanobenzoic acid.

The novel esters of Formula I can be produced in various ways using known methods for which the reaction conditions can be readily derived from the pertinent literature. For example, the esters of Formula I can be prepared by reacting a phenol of Formula II:

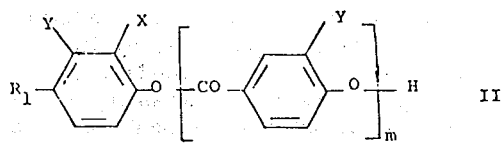

wherein $R_1$, X and Y have the above-indicated values and m is 0 or 1 with a substituted benzoic acid of Formula III

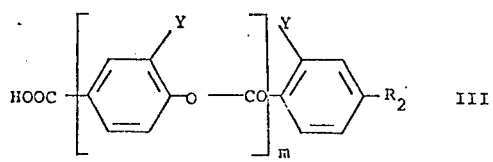

wherein $R_2$, Y and m have the above-identified values, and/or with a functional acid derivative thereof, e.g., an acid halide or acid anhydride, provided that in one of the compounds II or III, m = 0. Furthermore, on compounds of or analogous to Formula I wherein hydroxyl groups are present in place of and/or in the residues $R_1$ and $R_2$, these hydroxyl groups can be converted into alkoxyalkyl, alkoxy or alkoxyalkoxy residues in accordance with conventional etherifying methods.

The esterification can take place according to all known methods. Suitable functional acid derivatives include but are not limited to the acid halides, particularly the acid chlorides, or the corresponding anhydrides. The esters of Formula I are obtained by reaction with a phenol of Formula II, preferably in the presence of an alkaline or Lewis base catalyst, e.g., NaOH, KOH, $Na_2CO_3$, $K_2CO_3$, triethylamine, or pyridine. An excess of the phenol is frequently employed, and the reaction is carried out at temperatures between 0° C. and the boiling temperature of the reaction mixture. Phenols of Formula II or the alkali metal phenolates thereof can also be reacted with halides or anhydrides of the acids III to be esterified, with or without the addition of an acid-neutralizing substance, e.g., sodium hydroxide, potassium hydroxide, sodium carbonate, potassium carbonate or pyridine. The reaction can be effected in inert, preferably aprotic organic solvents, customarily ether, tetrahydrofuran or benzene.

The required starting materials of Formulae II and III are conventional or can be produced analogously to known compounds in accordance with standard methods. For example, with phenols analogous to those of Formula II, wherein m = 0 but which do not contain the substituent X, this latter substituent can be introduced in accordance with conventional methods, e.g., these phenols are brominated, the OH-group is blocked by a masking group (for example, the acetyl residue), and the reaction is conducted in an inert, preferably aprotic, organic solvent (e.g., dimethylformamide, hexamethylphosphoric triamide, pyridine, dimethyl sulfoxide, or acetonitrile) with copper (I) cyanide. The masking group is subsequently split off by hydrolysis.

The phenols of Formula II are also obtainable from the corresponding aldehydes, wherein a —CHO-group is present in place of the CN-group. This —CHO-group can be conveniently converted into a —CN-group by reaction with hydroxylamine and subsequent splitting off of water. The aldehydes, in turn, are readily available from the corresponding phenols by reaction with chloroform and alkali or with substituted formamides in the presence of phosgene or phosphorus oxychloride. Finally, the phenols of Formula II with a cyano group can also be produced from the corresponding salicylic acid amides by splitting off water (for example by means of $P_2O_5$, $PCl_5$ or sulfuric acid).

The nitro group is readily introduced by treating the corresponding phenols with nitric acid. Preferably, the phenol is added dropwise to aqueous nitric acid, and the reaction is followed by a steam distillation step.

The thus-obtained phenols wherein m = 1 can thereafter be reacted with correspondingly substituted p-hydroxybenzoic acids and/or the functional derivatives thereof.

The acids of Formula III are either readily obtainable p-substituted benzoic acids or, for those in which m = 1, they can be easily formed by esterification of 4-hydroxybenzaldehydes with the correspondingly substituted benzoic acids and/or the chlorides thereof; the thus-produced aldehyde is subsequently oxidized to the acid with an oxidizing agent (e.g., atmospheric oxygen, hydrogen peroxide, chromium oxide, potassium permanganate). It is also possible to prepare the acid of Formula III wherein $m = 1$ by direct esterification of 4-hydroxybenzoic acids with the correspondingly substituted benzoic acids.

Etherification methods known from the literature can be employed for the introduction of alkyl substituents into those compounds analogous to those of Formula I, but containing hydroxyl groups instead of or within the residues $R_1$ and/or $R_2$. The reaction with the corresponding alkyl halides under alkaline conditions is particularly simple. The reaction is normally conducted in an inert organic solvent and at elevated temperatures up to the boiling point of the solvent used. The required alkali is added most simply in the form of alkali hydroxides, e.g., NaOH, KOH or LiOH, however, other reactants customary for etherification reactions can also be utilized.

Those skilled in the art will have no difficulties in selecting the mode of operation which is simplest for preparing a specific ester of Formula I; generally, the immediate accessability of available starting materials will be a decisive factor. The reaction conditions are familiar to any chemist working in the synthesis field.

The addition of 1–35% by weight, preferably 5–15% by weight of one or more esters of Formula I to nematic substances in accordance with this invention has quite a number of surprising advantages. For example, the activating times are substantially shortened since the strong dipole component acting perpendicular to the longitudinal axes of the molecules facilitates, after switching on the operating voltage, a rearrangement of the vertically oriented nematic substances into a position parallel to the electrode surface. Also, the operating voltages themselves can be reduced. The larger the proportion of an ester of Formula I, the smaller are the operating voltages which must be selected. However, in particular, the effects of light on the switching times and the threshold voltage of the dynamic scattering and other field-dependent effects are compensated. Since the esters of Formula I themselves exhibit nematic characeristics, they broaden the nematic range of the eutectic produced with the aid thereof, which is of considerable advantage in many fields of application.

Suitable nematic substances are all those which have also heretofore been utilized or are usable in electro-optical indicator devices due to their liquid-crystalline characteristics. The most customary substances consist of mixturs of derivatives from the series of the azobenzenes, azoxybenzenes, Schiff bases, particularly benzylidene derivatives, phenylbenzoates, optionally halogenated stilbenes, diphenylacetylene derivatives, diphenylnitrons, and substituted cinnamic acids. In general, isomeric pairs and/or eutectic mixtures are employed.

The modification of nematic substances in accordance with this invention is advantageous especially for nematic compositions containing azoxybenzene derivatives, since the yellow color of indicator devices produced with such liquid crystals is considerably lessened by the additive of the present invention.

The novel compounds of Formula I show another surprising effect. It has been disclosed in U.S. application Ser. No. 277,502 filed Aug. 3, 1972 and in Angewandte Chemie 84: 636 (1972) that a number of substituted phenyl esters of benzoyloxybenzoic acid, though devoid of dynamic scattering due to their positive dielectric anisotropy, possess other properties of interest in this connection. It is now surprisingly possible, by adding esters of Formula I in accordance with this invention, to reverse the arithmetic sign of the dielectric anisotropy so that then also these compounds, in a mixture with the esters of Formula I are capable of dynamic scattering.

Preferably, the novel esters are added to other nematic substances in such an amount that they form eutectic mixtures with the substances constituting the nemaic phase. In very many cases, this is achieved by adding approximately 10% by weight of an ester of Formula I to nematic substances, particularly those based on nematic azoxybenzene derivatives. Furthermore, considering the solubility in the nematic phases to be modified, those esters of Formula I are preferred which have low melting points, preferably below 100° C.

The most important components of the conventional nematic substances can be characterized by the general Formula IV

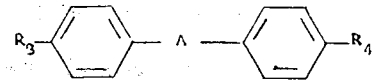

wherein A is one of

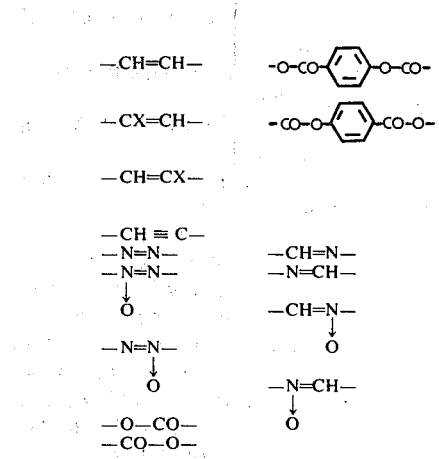

X' is a halogen atom, preferably a chlorine atom, and $R_3$ and $R_4$ are each alkyl, alkoxy, or alkanoyloxy residues of up to 18, preferably up to 8 carbon atoms.

In most of these compounds, $R_3$ and $R_4$ are peferably different, wherein one of the residues in most cases is an alkyl group and the other an alkoxy or alkanoyloxy group. However, all other variants of the provided substituents are also customary. Quite a number of such nematic substances are already commercially available.

Frequently, the nematic phases are modified by the addition of cholesteric compounds in order to obtain memory effects. Such additions of cholesteric phases range generally around approximately 10% by weight. Such memory nematic phases are likewise suitable in this invention. A number of other suitable nematic phases are described, for example in published German Patent Application P 19 51 092 and in the aforementioned U.S. Patent Applications.

It is particularly advantageous to add the esters of Formula I to those nematic substances which exhibit, due to a special modification, a particularly satisfactory vertical orientation. Such modified nematic mixtures are disclosed, for example, in U.S. Pat. application Ser. No. 334,603. The carboxylic acids to be added to that invention are characterized by a carboxyl group in conjugation to a phenyl ring carrying an elongated residue in the p-position. They can be characterized by Formula V:

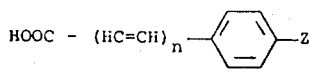     V wherein

Z is $-R_5$ or 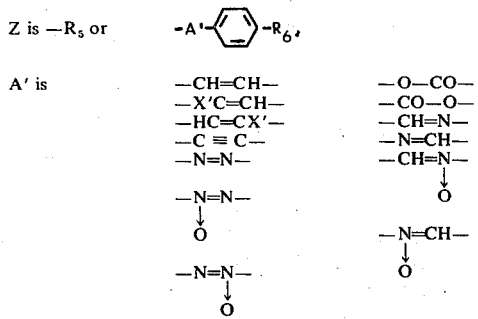

| A' is | | |
|---|---|---|
| $-CH=CH-$ | | $-O-CO-$ |
| $-X'C=CH-$ | | $-CO-O-$ |
| $-HC=CX'-$ | | $-CH=N-$ |
| $-C\equiv C-$ | | $-N=CH-$ |
| $-N=N-$ | | $-CH=N-\!\!\downarrow\!\!O$ |
| $-N=N-\!\!\downarrow\!\!O$ | | $-N=CH-\!\!\downarrow\!\!O$ |
| $-N=N-\!\!\downarrow\!\!O$ | | |

$R_5$ is alkyl of 6-18 carbon atoms or alkoxy or alkanoyloxy of 4-18 atoms, $R_6$ is alkyl, alkoxy or alkanoyloxy of 1-18 carbon atoms, $X'$ is halogen, preferably Cl, and $n$ is 0 or 1, with the provision that $R_5 = R_6$ if $n = 1$.

In many cases, it is advantageous to employ at least a portion, e.g., at least 1% of the acids of Formula V in the form of salts thereof. Simultaneously with the perpendicular orientation, a modification of the conductivity is likewise provided so that the specific electric resistance required for a good reproducibility of the dynamic scattering effect can be adjusted as desired. The only requirement for selecting such salts is that the ionization potential thereof is lower than the field strengths to be encountered in the nematic system being employed. Preferred are large, bulky cations.

Basically, all those salts can be employed which exhibit sufficient solubility in the particular nematic phases being used and which do not yield any protons, i.e., are aprotic. In addition to the alkali metal salts Na, K, Li, Rb and Cs and the alkaline earth metal salts Ca, Sr and Ba, especially suitable are quaternary ammonium and/or phosphonium salts in which all ligands are occupied by organic residues, preferably by alkyl or pheyl residues. Free H-ions are undesirable since they would interfere with the intended utilization of the system. Suitable substituents in these ammonium and/or phosphonium cations include but are not limited to linear or branched alkyl of 1-18 carbon atoms and phenyl. Quaternary ammonium compounds having a great variety of alkyl residues are commercially available since they are widely utilized, inter alia, in the detergent industry. Among the phosphonium salts, the most well-known are those which are obtained from triphenylphospine or trialkylphosphines by reaction with alkyl halides.

Suitable quaternary ammonium cations include but are not limited to those of the formula $(R_4)_4N^+$ wherein $R_4$ is an alkyl of 1-8 carbon atoms, preferably linear alkyl, e.g., tetramethylammonium, tetraethylammonium, tetrapropylammonium, tetrabutylammonium, tetrapentylammonium, tetrahexylammonium, and tetraheptylammonium;

those of the formula $(R_4)_3R_5N^+$ or $(R_4)_2(R_5)_2N^+$ or $(R_4)_2R_5R_6N^+$ wherein $R_4$ is as defined above and $R_5$ and $R_6$ are different alkyl group as defined for $R_4$ or phenyl, e.g., tributylpropylammonium, triethylmethylammonium, triethylpropylammonium, trimethylphenylammonium and ethyldodecyldimethylammonium; and other quaternary ammonium salts, e.g., cetyltrimethylammonium, octadecyltrimethylammonium and tetraphenylammonium. Of these, preferred are tetraphenylammonium and ethyldodecyldimethylammonum.

Suitable commercially available phosphonium cations include but are not limited to tetraphenylphosphonium, triphenylisopropylphoshonium, trioctylhexylphosphonium, tributyldodecylphosphonium and tributyloctadecylphosphonium.

Solutions of the acids of Formula V and/or the salts thereof in nematic phases are distinguished by being capable, when introduced between two defining surfaces, of forming completely transparent, glass-clear layers wherein the molecules are positioned with their longitudinal axes perpendicular to the defining surfaces, i.e., they exhibit homotropous behavior. The orientation effect of the acids of Formula V is surprisingly not limited to nematic phases of a similar structure, but is generally applicable, the only known prerequiste being that the acid and/or the salts thereof have a sufficiently high solubility in the nematic phase. Naturally, the more related to acids and/or the salts thereof are with the liquid crystals in their chemical structure, the higher the solubility therein. However, since even extraordinarily minor additions are sufficient to obtain the desired effect, solubility is hardly a restricting factor. It is normally desirable to employ the salts of Formula V in admixture with the free carboxylic acids, rather than the salts by themselves. The mixture ratio can be chosen arbitrarily; generally 0.01– 1 parts salt per part of the acid are used.

The boundary surfaces between which the modified nematic phases are to be introduced should be hydrophilic since it appears that an interaction occurs between the carboxyl function and the boundary surface. Thus, glass plates are particularly suitable, as are synthetic resins having surface hydrophilic groups, e.g., polysaccharides, especially cellulose derivatives such as "Celluloid". Also suitable as defining surfaces are plates coated partially or entirely with conductive layers. The most customary coatings of this type are made of tin dioxide applied, e.g., by reaction coating; however, other materials are likewise suitable, e.g., indium oxide or tin dioxide with antimony trioxide or mixtures of these materials. As is known, these conductive layers are frequently partially removed by etching to produce patterns which can be made visible by nematic liquid crystals. Of course, the dynamic scattering effect occurs only at those places where two conductive layers oppose each other. The layer thicknesses of the nematic phases between the defining surfaces are normally 5–40 microns, but this range is not critical or limiting. The display devices proper, their constructions, and their dimensions are conventional in the art.

Oriented layers can be produced in a display device by introducing the modified nematic phases either at temperatures above the transition or clearing point between the plate arrangement and then allowing the phases to cool; or alernatively by introducing the phases between the boundary surface arrangement at room temperature and then heating the arrangement briefly to a temperature which is at least several degrees above the transition point of the nematic phase employed. In both cases, therodynamically stable, perpendicularly oriented layers are obtained after cooling to room temperature.

Surprisingly, the tendency of these modified nematic phases to form perpendicularly oriented layers is so strong that the phases with a content of less than 2%, e.g., 0.001 – 2% and preferably 0.01 – 0.25% by weight of an acid of Formula V and the salts thereof already exhibit homotropous behavior when filling the plate arrangement at room temperature, so that a subsequent heating step to above the transition point can be eliminated. This technique is preferably utilized in cases where the defining boundary surfaces are uniform, e.g., when pure glass surfaces are provided, or no patterns have been etched into the conductive layers, or in case of clean heterogeneous surfaces.

The modified nematic phases of the present invention can be utilized in the same manner as the previously known phases, especially for optical display systems. They are suitable, for example, for the digital indication of measured data, results of electronic computers, the time of day, or process data, numerals, letters or other symbols. In addition to excellent perpendicular orientation, the novel compositions of this invention exhibit the special advantage of a short "dead time" upon activation.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight. The term "vertically oriented" in the follownng examples refers to the aforementioned perpendicular orientation when the indicator device is in a horizontal position.

EXAMPLE 1

90 g. of the eutectic mixture, melting at −5°, from the isomeric mixture of 4-n-butyl-4′-methoxyazoxybenzene/4′-n-butyl-4-methoxyazoxybenzene and the isomeric mixture of 4-ethyl-4′-methoxyazoxybenzene/4′-ethyl-4-methoxyazoxybenzene (t.p. +75°) is mixed with 10 g. of the (4′-n-butyl-2′-cyanophenyl) ester of 4-(4-n-hexyloxybenzoyloxy)-benzoic acid. This mixture has a melting point of −12° and a transition point of +85°.

With equal success, it is also possible to use, in place of this eutectic mixture, the isomeric mixture of 4-n-butyl-4′-methoxyazoxybenzene/4′-butyl-4-methoxyazoxybenzene, m.p. 16°, t.p. +75°.

In a layer having a thickness of 20 microns between two glass plates having a conductive coating of tin dioxide on the insides, the mixtures show full dynamic scattering even after 8 hours under irradiation with a UV lamp from a distance of 50 cm. at an operating voltage of 30 volts A.C. The same mixture without the addition of the ester, however, exhibits no longer any dynamic scattering already after 10 minutes under the same conditions.

EXAMPLE 2

A mixture of 90 g. of a eutectic mixture, melting at −5°, of the isomers 4-n-butyl-4′-methoxyazoxybenzene/4′-n-butyl-4-methoxyazoxybenzene and the isomers 4-ethyl-4′-methoxyazoxybenzene/4′-ethyl-4-methoxyazoxybenzene, additionally containing 90 mg. of 4-(4-methoxyphenylazoxy)-benzoic acid, is mixed with 10 g. of the (4′-n-butyl-2′-cyanophenyl) ester of 4-(4-n-hexyloxybenzoyloxy)-benzoic acid. This mixture has a melting point of −12° and a transition point of +83°.

The basic mixture, without the addition of the ester according to the invention, loses its operability when irradiated with UV light analogously to Example 1, whereas the mixture of the present invention remains unaffected.

In place of the above-mentioned ester, one or more of the following compounds can be utilized with equal success:

(4′-n-butyl-2′-cyanophenyl) ester of 4-(4-methoxybenzoyloxy)-benzoic acid, m.p. 129°, t.p. 181°;

(4′-n-butyl-2′-cyanophenyl) ester of 4-(4-ethoxyethoxybenzoyloxy)-benzoic acid, m.p. 88°, t.p. 112°;

(4′-n-butyl-2′-cyanophenyl) ester of 4-(4-n-butylbenzoyloxy)-benzoic acid, m.p. 90°, t.p. 121°;

(2′-cyano-4′-methoxyphenyl) ester of 4-(4-n-hexyloxybenzoyloxy)benzoic acid, m.p. 121°, t.p. 187°;

(2′-cyano-4′-methoxyphenyl) ester of 4-(4-methoxybenzoyloxy)benzoic acid, m.p. 203°, t.p. 237°;

(2′-cyano-4′-methoxyphenyl) ester of 4-(4-ethoxyethoxybenzoyloxy)-benzoic acid, m.p. 112°, t.p. 171°;

(2′-cyano-4′-methoxyphenyl) ester of 4-(4-n-butylbenzoyloxy)-benzoic acid, m.p. 132°, t.p. 171°;

(2′-cyano-4′-n-hexyloxyphenyl) ester of 4-(4-n-hexyloxybenzoyloxy)-benzoic acid, m.p. 79°, t.p. 159°;

(2′-cyano-4′-n-hexyloxyphenyl) ester of 4-(4-methoxybenzoyloxy)-benzoic acid, m.p. 136°, t.p. 191°;

(2′-cyano-4′-n-hexyloxyphenyl) ester of 4-(4-ethoxyethoxybenzoyloxy)-benzoic acid;

(2′-cyano-4′-n-hexyloxyphenyl) ester of 4-(4-n-butylbenzoyloxy)-benzoic acid, m.p. 100°, t.p. 148°;

(2′-cyano-4′-n-nonylphenyl) ester of 4-(4n-hexyloxybenzoyloxy)-benzoic acid, m.p. 65°, t.p. 135°;

(2′-cyano-4′-n-nonylphenyl) ester of 4-(4-methoxybenzoyloxy)-benzoic acid;

(2'-cyano-4'-n-nonylphenyl) ester of 4-(4-ethoxyethoxybenzoyloxy)-benzoic acid;
(240-cyano-4'-n-nonylphenyl) ester of 4-(4-n-butylbenzoyloxy)-benzoic acid;
(2'-cyano-4'-n-pentylphenyl) ester of 4-(4-methoxybenzoyloxy)-benzoic acid;
(2'-cyano-4'-n-pentylphenyl) ester of 4-(4-hexyloxybenzoyloxy)-benzoic acid, m.p. 77°, t.p. 153°;
(2'-cyano-4'-n-pentylphenyl) ester of 4-(4-etoxyethoxybenzoyloxy)-benzoic acid;
(2'-cyano-4'-n-pentylphenyl) ester of 4-(4-n-butylbenzoyloxy)-benzoic acid;
(4'-n-butyl-2'-nitrophenyl) ester of 4-(4-n-hexyloxybenzoyloxy)-benzoic acid;
(2',3'-dicyano-4'-methoxyphenyl) ester of 4-(4n-butylbenzoyloxy)-benzoic acid;
(4'-n-butyl-2'-cyanophenyl) ester of 4-(4-n-hexyloxybenzoyloxy)-3-cyanobenzoic acid;
(2''-cyano-4''-n-hexyloxyphenyl) ester of 4-(2'-cyano-4'-methoxybenzoyloxy)-benzoic acid;
(4''-n-butyl-2''-cyanophenyl) ester of 4-(2'-cyano-4'-hexyloxybenzoyloxy)-3-cyanobenzoic acid.

EXAMPLE 3

20 g. of the (2'-cyano-4'-pentylphenyl) ester of 4-(4-hexyloxybenzoyloxy)-benzoic acid is dissolved in a mixture of 40 g. of 4-n-butyl-4'-methoxyazoxybenzene (isomeric mixture), 40 g. of 4,4'-di-n-butylazoxybenzene, and 0.1 g. of 4-(4-hexyloxybenzoyloxy)-benzoic acid.

This mixture melts at −30°, becomes clear at +76°, and yields vertically oriented layers. In electrooptical indicator devices having a layer thickness of 25 microns, the threshold voltage necessary for the dynamic scattering effect remains unchanged even under the influence of UV radiation.

EXAMPLE 4

2.5 g. of p-hexyloxybenzoic acid (m.p. 109°, t.p. 152°), as well as 50 mg. of N-ethyl-N-dodecyl-N,N-dimethyl-ammonium-p'-hexyloxybenzoate are dissolved in 1000 g. of the eutectic mixture of Example 1, melting at −5°. This solution, with a specific electric resistance of $4 \cdot 10^{-9}$ Ω cm., has a conductivity optimal for the dynamic scattering effect. To this mixture is added 100 g. of (2'-cyano-4'-n-hexyloxyphenyl) ester of 4-(4-ethoxyethoxybenzoyloxy)-benzoic acid. Two rectangular glass plates having a size of approximately 50 cm² and carrying on at least one side a conductive layer of tin dioxide are placed upon each other so that the conductive layers face each other. On two opposed points, spacer elements of glass are disposed, so that a hollow space of a thickness of 25 microns is produced between the plates.

One drop of the above-mentioned solution, heated to 85°, is introduced into one of the two lateral openings of the electrode unit, which likewise has been heated to about 85°. The nematic liquid is uniformly distributed in the hollow space due to capillary forces. After cooling to temperatures of below 75° (to a temperature below the transition point of the nematic phase employed), a glass-clear nematic layer is obtained, of a completely vertical orientation, which is stable at room temperature. The effect of UV radiation on the switching times and the threshold voltage of the dynamic scattering is compensated.

The same results are attained if other carboxylic acids and/or the salts thereof, as described in U.S. Pat. Application Ser. No. 334,603, filed February 22, 1973, are added to the nematic substance. For example, an addition of 1.5 g. of 4-(4'-methoxyphenylazoxy)-benzoic acid proved to be advantageous.

EXAMPLE 5

8 g. of the (2'-cyano-4'-pentylphenyl) ester of 4-(4-hexyloxybenzoyloxy)-benzoic acid is added to a mixture of 61 g. of the 4-n-pentylphenyl ester of anisic acid and 31 g. of the 4'-n-pentylphenyl ester of 4-hexanoyloxybenzoic acid. The mixture has a melting point of −19° and a transition point of 54°.

A sandwich cell consisting of two rectangular superimposed glass plates having a size of about 8 cm² and coated on the inside with thin $SnO_2$ layers is heated to 80°. On two opposed sides, two spacer sheets of polyester are arranged between the glass plates, having a width of 1.5 mm. and a thickness of 20 microns. One of the two lateral openings is brought into contact with a drop of the above-described solution, likewise heated to 80°. By capillary forces, the liquid is evenly distributed between the two glass plates and forms, after cooling, a unidirectionally oriented layer which is stable at room temperature. The sandwich cell can also be filled at room temperature, and the solution need not be heated, either. Also in this case, uniformly transparent, vertically oriented nematic layers are produced, the switching times of which do not change even under the influence of light.

EXAMPLE 6

50 mg. of p-(p-methoxybenzoyloxy)-benzoic acid and 15 g. of the (2'-cyano-4'-nonylphenyl) ester of 4-(4-n-hexyloxybenzoyloxy)-benzoic acid are added to 100 g. of a 1:1 mixture of N-(p-methoxybenzylidene)-p-n-butylaniline and N-(p-ethoxybenzylidene)-p-n-butylaniline. With the aid of this solution, vertically oriented nematic layers are produced in accordance with the methods described in Examples 1–5.

EXAMPLE 7

8 mg. of p-hexanoyloxybenzoic acid (m.p. 152°) and 2 g. of the (2'-cyano-4'-hexyloxyphenyl) ester of 4-(4-ethoxyethoxybenzoyloxy)-benzoic acid are added to 10 g. of a eutectic mixture, melting at −3°, of N-(p-methoxybenzylidene)-p-n-butylaniline, N-(p-methoxybenzylidene)-p-butyryloxyaniline, and the p-ethoxyphenyl ester of p-hexanoyloxybenzoic acid. Analogously to Examples 1–5, vertically oriented, nematic thin layers are produced from this mixture.

EXAMPLE 8

5 mg. of 4-hexanoyloxybenzoic acid and 1 g. of the (2'-cyano-4'-pentylphenyl) ester of 4-(4-n-hexyloxybenzoyloxy)-benzoic acid are dissolved in a mixture of 9 g. of the eutectic mixture, melting at −22°, of the p-hexyloxyphenyl ester of p-n-butylbenzoic acid, the p'-n-butylphenyl ester of p-n-hexyloxybenzoic acid, the p'-hexyloxyphenyl ester of p-butyryloxybenzoic acid, and the p'-methoxyphenyl ester of p-butyryloxybenzoic acid, as well as 0.5 g. of cholesterol oleyl carbonate and 0.5 g. of cholesterol nonanoate. This solution, when processed analogously to Example 4, yields vertically oriented layers.

EXAMPLE 9

10 g. of a mixture of 66% by weight of d,1-4-(2-methylhexyl)-4'-ethoxy-α-chloro-trans-stilbene and 34% by weight of 4-n-heptyl-4'-ethoxy-α-chloro-trans-stilbene is mixed with 4 mg. of p-(p-butoxy-trans-stilbene)-carboxylic acid and 0.8 g. of the (4'-n-butyl-2'-cyanophenyl) ester of 4-(4-ethoxyethoxybenzoyloxy)-benzoic acid. This mixture, when used analogously to Example 1, 2, or 3, yields unidirectional, thin layers.

EXAMPLE 10

0.5 mg. of N-(p-ethoxyphenyl)-α-p-phenylnitroncarboxylic acid and 0.2 g. of the (4'-butyl-2'-cyanophenyl) ester of 4-(4-n-hexyloxybenzoyloxy)-benzoic acid are dissolved in 1 g. of a mixture of 65% by weight of N-(p-methoxyphenyl)-α-(p-hexyloxyphenyl)-nitron and 35% by weight of N-(p-methoxyphenyl)-α-(p-n-heptylphenyl)-nitron. This mixture forms vertically oriented layers in indicator devices.

EXAMPLE 11

A mixture composed of
33% 4-n-butylphenyl ester of anisic acid
22% 4'-methoxyphenyl ester of 4-n-butylbenzoic acid
22.5% (4-n-butylphenyl) ester of 4-(4-n-butylbenzoyloxy)-benzoic acid, and
22.5% (4'-n-butylphenyl) ester of 4-anisoyloxybenzoic acid
exhibits positive dielectric anisotropy and accordingly is not capable of dynamic scattering. By replacing in this mixture the 22.5% of the 4'-butylphenyl ester of 4-anisoyloxybenzoic acid by the same amount of the (4'-n-butyl-2'-cyanophenyl)ester of 4-(4-hexyloxybenzoyloxy)-benzoic acid, a mixture is obtained showing dynamic scattering in electrooptical indicator devices.

PREPARATION OF THE ESTERS OF FORMULA I

EXAMPLE A 29 g. of 4-n-butyl-2-cyanophenol is dissolved in 300 cc. of absolute benzene and mixed with 14 cc. of absolute pyridine. Under agitation, the mixture is heated to the boiling point, and while heating, a solution of 59.8 g. of 4-(4-hexyloxybenzoyloxy)-benzoic acid chloride is added dropwise thereto within 30 minutes. The reaction mixture is refluxed for 3 hours, allowed to cool, and the thus-precipitated pyridinium hydrochloride is filtered off. The filtrate is washed twice with 200 cc. of water, dried, and concentrated by evaporation. The residue is crystallized from ethanol until the melting and transition points are constant. The product is the (4'-n-butyl-2'-cyanophenyl) ester of 4-(4-hexyloxybenzoyloxy)-benzoic acid, m.p. 96°, t.p. 149°.

With the use of the correspondingly substituted phenols, on the one hand, and the benzoic acid chlorides, on the other hand, the following compounds are analogously obtained:

(4'-n-butyl-2'-cyanophenyl) ester of 4-(4-methoxybenzoyloxy)-benzoic acid, m.p. 129°, t.p. 181°;
(4'-n-butyl-2'-cyanophenyl) ester of 4-(4-ethoxyethoxybenzoyloxy)-benzoic acid, m.p. 88°, t.p. 112°;
(4'-n-butyl-2'-cyanophenyl) ester of 4-(4-n-butylbenzoyloxy)-benzoic acid, m.p. 90°, t.p. 121°;
(2'-cyano-4'-methoxyphenyl) ester of 4-(4-n-hexyloxybenzoyloxy)-benzoic acid, m.p. 121°, t.p. 187°;
(2'-cyano-4'-methoxyphenyl) ester of 4-(4-methoxybenzoyloxy)-benzoic acid, m.p. 203°, t.p. 237°;
(2'-cyano-4'-methoxyphenyl) ester of 4-(4-ethoxyethoxybenzoyloxy)-benzoic acid, m.p. 112°, t.p. 171°;
(2'-cyano-4'-methoxyphenyl) ester of 4-(4-n-butylbenzoyloxy)-benzoic acid, m.p. 132°, t.p. 171°;
(2'-cyano-4'-n-hexyloxyphenyl) ester of 4-(4-n-hexyloxybenzoyloxy)-benzoic acid, m.p. 79°, t.p. 159°;
(2'-cyano-4'-n-hexyloxyphenyl) ester of 4-(4-methoxybenzoyloxy)-benzoic acid, m.p. 136°, t.p. 191°;
(2'-cyano-4'-n-hexyloxyphenyl) ester of 4-(4-ethoxyethoxybenzoyloxy)-benzoic acid;
(2'-cyano-4'-n-hexyloxyphenyl) ester of 4-(4-n-butylbenzoyloxy)-benzoic acid m.p. 100°, t.p. 148°;
(2'-cyano-4'-n-nonylphenyl) ester of 4-(4-n-hexyloxybenzoyloxy)-benzoic acid, m.p. 65°, t.p. 135°;
(2'-cyano-4'-n-nonylphenyl) ester of 4-(4-methoxybenzoyloxy)-benzoic acid;
(2'-cyano-4'-n-nonylphenyl) ester of 4-(4-ethoxyethoxybenzoyloxy)-benzoic acid;
(2'-cyano-4'-n-nonylphenyl) ester of 4-(4-n-butylbenzoyloxy)-benzoic acid;
(2'-cyano-4'-n-pentylphenyl) ester of 4-(4-methoxybenzoyloxy)-benzoic acid;
(2'-cyano-4'-n-pentylphenyl) ester of 4-(4-hexyloxybenzoyloxy)-benzoic acid, m.p. 77°, t.p. 153°;
(2'-cyano-4'-n-pentylphenyl) ester of 4-(4-ethoxyethoxybenzoyloxy)-benzoic acid;
(2'-cyano-4'-n-pentylphenyl) ester of 4-(4-n-butylbenzoyloxy)-benzoic acid;
(4'-n-butyl-2'-nitrophenyl) ester of 4-(4-n-hexyloxybenzoyloxy)-benzoic acid;
(2', 3'-dicyano-4'-methoxyphenyl) ester of 4-(4-n-butylbenzoyloxy)-benzoic acid;
(4'-n-butyl-2'-cyanophenyl) ester of 4-(4-n-hexyloxybenzoyloxy)-3-cyanobenzoic acid;
(2''-cyano-4''-n-hexyloxyphenyl) ester of 4-(2'-cyano-4'-methoxybenzoyloxy)-benzoic acid;
(4''-n-butyl-2''-cyanophenyl) ester of 4-(2'-cyano-4'-hexyloxybenzoyloxy)-3-cyanobenzoic acid.

EXAMPLE B 17.7 g. of the potassium salt of the (2'-cyano-4'-hexyloxyphenyl) ester of 4-hydroxybenzoic acid and 7 g. of sodium bicarbonate are suspended in 400 cc. of diethyl ether at −10°. Under agitation and cooling, a solution of 8.2 g. of anisic acid chloride in 100 cc. of diethyl ether is added dropwise so that the temperature does not rise above −10°. After this solution has been added, the reaction mixture is heated to +20° and further stirred for 15 minutes at this temperature. Then, the ether solution is filtered, washed with aqueous sodium bicarbonate solution and water, and dried over sodium sulfate. After the ether has been distilled off, the (2'-cyano-4'-hexyloxphenyl) ester of (4-(4-methoxybenzoyloxy)-benzoic acid is recrystallized from ethyl acetate until the melting and transistion points are constant; m.p. 136°, t.p. 191°.

The esters set forth in Example A are likewise produced in an analogous manner wherein, in place of the potassium salts, the Na- and Li-salts can also be utilized, for example.

The required starting materials are available, for example, in accordance with the following methods:

I. Preparation of the Phenols of Formula IV a. 75 g. of 4-n-butylphenol is dissolved in 1000 cc. of carbon tetrachloride. 46 g. of solid sodium bicarbonate is added to this solution and, under ice water cooling, a solution of 80 g. of bromine in 200 cc. of carbon tetrachloride is added dropwise thereto. After a reaction time of 1 hour, the mixture is filtered off from inorganic salts, the filtrate is washed neutral, evaporated, and the residue is distilled. The fraction going over at 110°/0.2 torr is 2-bromo-4-n-butylphenol. The latter is dissolved in 44 g. of acetic anhydride, mixed with 10 drops of concentrated sulfuric acid, and refluxed for 5 hours. Subsequently, the reaction mixture is poured onto ice water, extracted with ether, the ether washed neutral, and distilled. At 113°/0.1 torr, the 2-bromo-4-n-butylphenyl ester of acetic acid passes over. 14 g. of this intermediate product is heated in 14 cc. of absolute pyridine and 1.3 cc. of acetonitrile, together with 5.35 g. of copper (I) cyanide for 52 hours at a bath temperature of 240°. The solution, cooled to about 90°, is then stirred into a mixture of 21 g. of iron (III) chloride, 5.5 cc. of concentrated hydrochloric acid, and 31.5 cc. of water, the mixture is heated for 20 minutes to 60°, and then the product is extracted with benzene. The benzene solution is washed neutral, dried, and distilled. The product, which is the 4-n-butyl-2-cyanophenyl ester of acetic acid, boils at 140°/0.1 torr. Thereafter, 9.05 g. of this intermediate product is refluxed for 4 hours in a solution of 2.8 g. of potassium hydroxide in 20 cc. of ethanol and 7 cc. of water. The alcohol is distilled off, 30 cc. of water is added, and the mixture is acidified with HCl under ice cooling, thus obtaining the product in an oily form. The product is taken up in ether, washed, dried, and freed of the solvent. For purification purposes, the compound is recrystallized from a mixture of 20 parts of benzene and 80 parts of petroleum ether (50/70), thus obtaining 4-n-butyl-2-cyanophenol, m.p. 60.5°.

Analogously, further phenols suitable for preparing the esters of this invention are also produced, for example:

| | |
|---|---|
| 2-cyano-4-methoxyphenol | m.p. 139° |
| 2-cyano-4-hexyloxyphenol | m.p. 96° |
| 2-cyano-4-n-pentylphenol | m.p. 81° |
| 2-cyano-4-n-heptylphenol | |
| 2-cyano-4-n-nonylphenol | m.p. 79.5° | b. 0.5 g. of triethylbenzylammonium chloride is added to a solution of 24.2 g. of 4-n-butylphenol in 100 cc. of chloroform; with ice, the reaction mixture is cooled to about 15°. 150 cc. of 50% strength sodium hydroxide solution is gradually added dropwise thereto, and the mixture is stirred for 3 hours at 10°. Then, the temperature is elevated to 60°, during which step the flask is equipped with a distillation bridge in order to distil off any excess chloroform. Thereupon, the solution is neutralized with dilute hydrochloric acid under ice cooling and then sujected to a stream distillation, during which 2-hydroxy-5-n-butylbenzaldehyde passes over as a light-yellow oil. 19.5 g. of this intermediate product is refluxed for 2 hours together with 8.8 g. of hydroxylammonium chloride, 14.9 g. of sodium formate, and 80 cc. of formic acid. Then, the formic acid is distilled off, 100 cc. of water is added, and the mixture is extracted with ether.

The ether solution is washed neutral, dried, and evaporated. The residue is distilled, wherein the product goes over at 120°/0.01 torr and crystallizes in the receiver. Subsequently, the product is recrystallized from petroleum ether/benzene, 4:1, thus obtaining 4-n-butyl-2-cyanophenol, m.p. 61°.

Also the other phenols required for producing the nematic esters of this invention are analogously produced.

c. 17.5 g. of sodium p-n-butylphenolate is introduced in finely pulverized form into an autoclave, under 8 atmospheres of carbon dioxide pressure. The reaction charge is heated to 180° for 24 hours, during which period carbon dioxide is occasionally introduced to maintain the pressure. The mixture is then allowed to cool, expanded, and 5-n-butyl-2-hydroxybenzoic acid is precipitated therefrom, which product is filtered, dried, and melted together with urea, so that the amide of the acid is formed. 9.6 g. of this acid amide is mixed in a mortar with 10.4 g. of phosphorus pentachloride, and the charge, after liquefaction, is poured into a distillation flask.

The thus-formed phosphorus oxytrichloride is distilled off under reduced pressure (about 20 torr) and finally the product is fractionated, which passes over at 142°/0.25 torr. Lastly, the 4-n-butyl-2-cyanophenol is crystallized from benzene/petroleum ether (1:4), m.p. 60°.

The other phenols of Formula IV wherein $m = 0$, necessary for producing the nematic esters of Formula I, can also be prepared analogously.

II. Preparation of the Benzoic Acids of Formula V a. 12.2 g. of 4-hydroxybenzaldehyde is dissolved with 50 cc. of 2N sodium hydroxide solution in 150 cc. of acetone. At room temperature, a solution of 25 g. of 4-hexyloxybenzoic acid chloride in 50 cc. of acetone is added dropwise thereto. After 2 hours, 350 cc. of water is added, thus precipitating the intermediate product 4-(4-hexyloxybenzoyloxy)-benzaldehyde. The latter is recrystallized from methanol, dried, and dissolved in 70 cc. of 90% acetic acid. To this mixture is added dropwise a solution of 19 g. of chromium (VI) oxide in 38 cc. of 60% strength acetic acid at room temperature. Thereafter, the mixture is agitated for 12 hours at 40°, 200 cc. of water is added, the thus-precipitated 4-(4-hexyloxybenzoyloxy)-benzoic acid is filtered, dried, and recrystallized from ethanol, m.p. 161°, t.p. 235°.

The other benzoic acids of Formula V are also produced in a corresponding mode of operation, which acids are required to produce the nematic esters; for example:

| | |
|---|---|
| 4-(4-n-butylbenzoyloxy)-benzoic acid | m.p. 192°, t.p. 241° |
| 4-anisoyloxybenzoic acid | m.p. 213°, t.p. 254° |
| 4-(4-ethoxyethoxybenzoyloxy)-benzoic acid | m.p. 155°, t.p. 214° | b. 1.38 g. of 4-hydroxybenzoic acid is dissolved in 50 cc. of pyridine and mixed at −10° dropwise with a solution of 2.4 g. of 4-hexyloxybenzoic acid chloride in 10 cc. of diethyl ether. The reaction mixture is refluxed for 4 hours, the solvents are distilled off, the remainder is taken up in 50 cc. of ether, and shaken neutral with dilute hydrochloric acid and then with water. After drying, the ether is removed by evaporation, the solid residue is dissolved in chloroform, mixed with a few drops of ether, and filtered over kieselguhr. Thereafter, by fractional crystallization, with the addition of 6 cc. of ethanol, 4-(4-hexylbenzoyloxy)-benzoic acid is obtained, which is recrystallized from ethanol, m.p. 162°, t.p. 235°.

Also according to this process, the acids of Formula V can be generally produced.

EXAMPLE C 3.89 g. of the 2'-cyano-4'-methoxyphenyl) ester of 4-(4-hydroxybenzoyloxy)-benzoic acid is dissolved in 100 cc. of dimethylformamide and mixed with 1.6 g. of ethoxyethyl bromide. 5 cc. of 2N sodium hydroxide solution is added to this reaction mixture, and the latter is heated under agitation. The mixture is maintained for 3 hours at an internal temperature of 115°. Then, the mixture is allowed to cool and poured onto 1 kg. of ice water, then stirred, and the precipitated product is filtered. The (2'-cyano-4'-methoxyphenyl) ester of 4-(4-ethoxyethoxybenzoyloxy)-benzoic acid is dried and recrystallized from ethanol, m.p. 112°, t.p. 171°.

In the same manner, 4.6 g. of the (4'-n-butyl-2'-cyanophenyl) ester of 4-(4-hydroxyethoxybenzoyloxy)-benzoic acid is reacted with 1.1 g. of ethyl bromide, thus likewise obtaining the aforementioned ester, m.p. 112°.

The remaining esters of Formula I wherein $R_1$ or $R_2$ is an alkoxy, alkoxyalkyl or alkoxyalkoxy group can likewise be produced analogously.

EXAMPLE D 4.55 g. of the (4'-n-butyl-2'-cyanophenyl) ester of 4-(4-hydroxybenzoyloxy)-benzoic acid is dissolved in 50 cc. of 1-hexanol with 1.65 g. of 1-bromohexane. This solution is heated to 80° and combined dropwise under agitation with 10 cc. of 1N sodium hydroxide solution. The mixture is allowed to react at 100° for 1 hour, then cooled to 40° and the solvent distilled off. The residue is mixed with 100 cc. of water and the thus-precipitated (4'-n-butyl-2'-cyanophenyl) ester of 4-(4-hexyloxybenzoyloxy)-benzoic acid is filtered, dried, distilled, and recrystallized from ethanol, m.p. 96°, t.p. 150°.

The remaining esters of Formula I wherein $R_1$ or $R_2$ is alkoxy, alkoxyalkyl or alkoxyalkoxy can likewise be produced analogously.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A nematic compound of the formula:

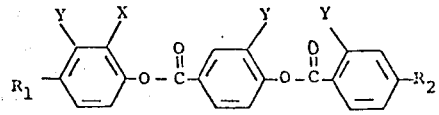

wherein $R_1$ and $R_2$ are each alkyl, alkoxyalkyl, alkoxy or alkoxyalkoxy of up to 10 carbon atoms; X is CN or $NO_2$; and Y is H or X.

2. A compound according to Claim 1 wherein X is CN.

3. A compound according to Claim 1 wherein Y is H.

4. A compound according to Claim 1 wherein at least one of $R_1$ and $R_2$ is straight chain alkyl of 1–10 carbon atoms.

5. A compound according to Claim 1 wherein at least one of $R_1$ and $R_2$ is straight chain alkoxy of 1–10 carbon atoms.

6. A compound according to Claim 1 wherein at least one of $R_1$ and $R_2$ is a branched alkyl or alkoxy wherein the carbon atom thereof directly joined to the phenyl ring bears two hydrogen atoms.

7. A compound according to Claim 1 wherein at least one of $R_1$ and $R_2$ is straight chain alkoxyalkoxy of two or more identical alkoxy units.

8. A compound according to claim 1 selected from the group consisting of (4'-n-butyl-2'-cyanophenyl) ester of 4-(4-n-hexyloxybenzoyloxy)-benzoic acid; (2'-cyano-4'-n-pentylphenyl) ester of 4-(4-n-hexyloxybenzoyloxy)-benzoic acid; and (2'-cyano-4'-n-hexyloxyphenyl) ester of 4-(4-n-hexyloxybenzoyloxy)-benzoic acid.

* * * * *